US009057710B2

(12) United States Patent
Hatcher et al.

(10) Patent No.: US 9,057,710 B2
(45) Date of Patent: Jun. 16, 2015

(54) SYSTEM AND METHOD FOR AUTOMATED OPTICAL INSPECTION OF INDUSTRIAL GAS TURBINES AND OTHER POWER GENERATION MACHINERY

(75) Inventors: Clifford Hatcher, Orlando, FL (US); Forrest R. Ruhge, Orlando, FL (US); Dennis H. Lemieux, Casselberry, FL (US); Himanshu Bhatnagar, Charlotte, NC (US); Yakup Genc, Dayton, NJ (US); Richard Hatley, Morristown, NJ (US)

(73) Assignee: Siemens Energy, Inc., Orlando, FL (US)

( * ) Notice: Subject to any disclaimer, the term of this patent is extended or adjusted under 35 U.S.C. 154(b) by 335 days.

(21) Appl. No.: 13/362,417

(22) Filed: Jan. 31, 2012

(65) Prior Publication Data

US 2013/0194413 A1    Aug. 1, 2013

(51) Int. Cl.
*H04N 7/18* (2006.01)
*G01N 21/954* (2006.01)
*G02B 23/24* (2006.01)
*H04N 5/225* (2006.01)

(52) U.S. Cl.
CPC .......... *G01N 21/954* (2013.01); *G02B 23/2476* (2013.01); *H04N 7/183* (2013.01); *H04N 2005/2255* (2013.01)

(58) Field of Classification Search
CPC ..... G02B 23/2476; H04N 7/18; H04N 7/183; G01N 21/954
USPC .......................................................... 348/82
See application file for complete search history.

(56) References Cited

U.S. PATENT DOCUMENTS

| 5,102,221 | A | 4/1992 | Desgranges et al. |
| 5,164,826 | A | 11/1992 | Dailey |
| 5,349,850 | A | 9/1994 | Young |
| 6,317,387 | B1 * | 11/2001 | D'Amaddio et al. ......... 367/129 |
| 6,992,315 | B2 | 1/2006 | Twerdochlib |
| 7,068,029 | B2 | 6/2006 | Hatcher et al. |
| 7,489,811 | B2 | 2/2009 | Brummel et al. |

(Continued)

FOREIGN PATENT DOCUMENTS

EP    0907077 A2    4/1999

OTHER PUBLICATIONS

Co-pending United States utility patent application entitled "System and Method for Automated Optical Inspection of Industrial Gas Turbines and Other Power Generation Machinery With Multi-Axis Inspection Scope", filed Jan. 31, 2012 and assigned U.S. Appl. No. 13/362,352.

(Continued)

*Primary Examiner* — Dave Czekaj
*Assistant Examiner* — Mohammad J Rahman

(57) ABSTRACT

Internal components of power generation machinery, such as gas and steam turbines are inspected with an optical camera inspection system that is capable of automatically positioning the camera field of view (FOV) to an area of interest within the machinery along a pre-designated navigation path and capturing images without human intervention. Automatic camera positioning and image capture can be initiated automatically or after receipt of operator permission. The pre-designated navigation path can be defined by operator manual positioning of an inspection scope within the power machine or a similar one of the same type and recording of positioning steps for future replication. The navigation path can also be defined by virtual simulation.

20 Claims, 17 Drawing Sheets

(56) References Cited

U.S. PATENT DOCUMENTS

| | | |
|---|---|---|
| 7,956,326 B1 | 6/2011 | Kychakoff et al. |
| 2004/0051525 A1 | 3/2004 | Hatcher et al. |
| 2004/0193016 A1* | 9/2004 | Root et al. .................. 600/146 |
| 2005/0199832 A1 | 9/2005 | Twerdochlib |
| 2006/0088793 A1 | 4/2006 | Brummel et al. |
| 2007/0129604 A1 | 6/2007 | Hatcher et al. |
| 2007/0157733 A1 | 7/2007 | Litzenberg et al. |
| 2007/0296964 A1 | 12/2007 | Nishimura et al. |
| 2011/0267428 A1 | 11/2011 | George et al. |
| 2012/0154594 A1 | 6/2012 | Xie et al. |
| 2012/0281084 A1 | 11/2012 | Hatcher et al. |
| 2013/0194412 A1 | 8/2013 | Hatcher et al. |
| 2013/0194413 A1 | 8/2013 | Hatcher et al. |
| 2014/0168420 A1* | 6/2014 | Naderhirn et al. ............ 348/128 |

OTHER PUBLICATIONS

Co-pending United States utility patent application entitled "System and Method for Automated Optical Inspection of Industrial Gas Turbines and Other Power Generation Machinery With Articulated Multi-Axis Inspection Scope", filed Jan. 31, 2012 and assigned U.S. Appl. No. 13/362,387.

* cited by examiner

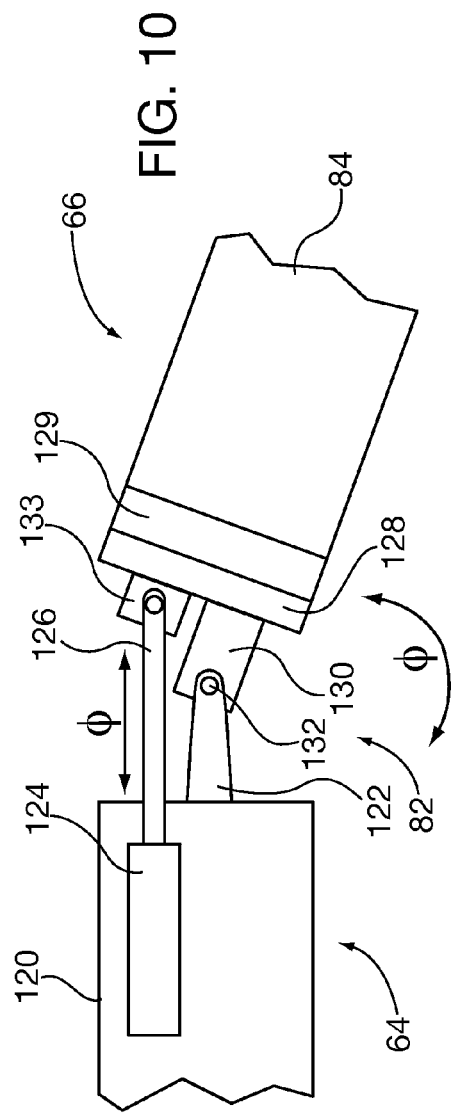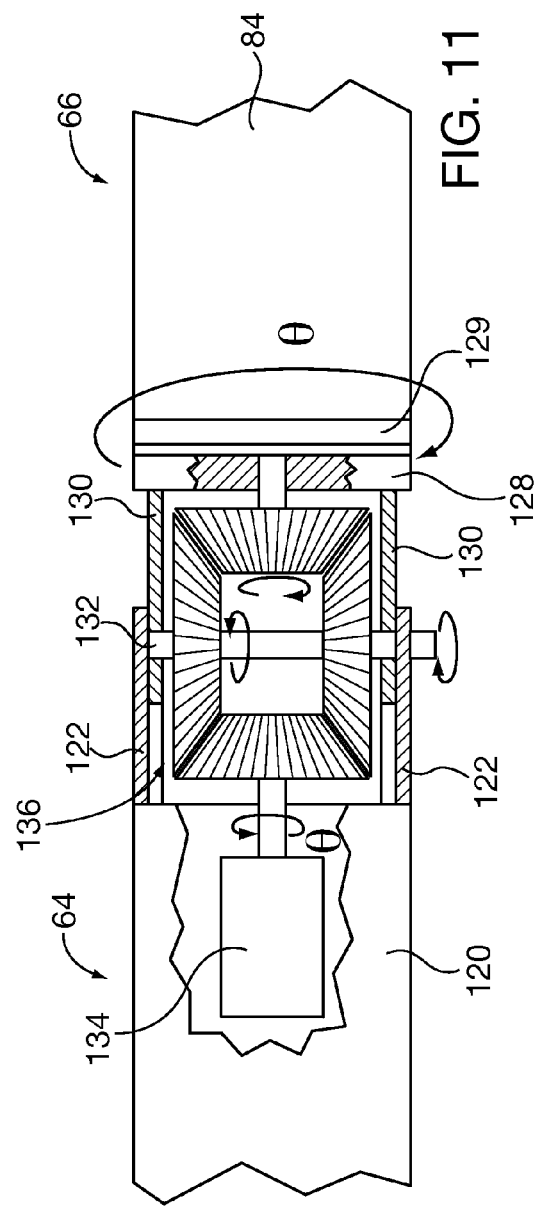

SYSTEM AND METHOD FOR AUTOMATED OPTICAL INSPECTION OF INDUSTRIAL GAS TURBINES AND OTHER POWER GENERATION MACHINERY

REFERENCE TO CO-PENDING APPLICATIONS

This application claims the benefit of co-pending United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/363,352, and co-pending United States utility patent application entitled "System And Method For Automated Optical Inspection Of Industrial Gas Turbines And Other Power Generation Machinery With Articulated Multi-Axis Inspection Scope", filed Jan. 31, 2012 concurrently herewith and assigned Ser. No. 13/362,387, all of which are incorporated by reference herein.

BACKGROUND OF THE DISCLOSURE

1. Field of the Invention

The invention relates to optical camera systems for nondestructive internal inspection of industrial gas turbines and other power generation machinery, including by way of non-limiting example steam turbines and generators. More particularly the invention relates to an optical camera inspection system that is capable of automatically positioning the camera field of view (FOV) to an area of interest within the machinery and capturing images without human intervention. Automatic camera positioning and image capture can be initiated automatically or after receipt of operator permission.

2. Description of the Prior Art

Power generation machinery, such as steam or gas turbines, are often operated continuously with scheduled inspection and maintenance periods, at which time the turbine is taken off line and shut down. By way of example, a gas turbine engine often will be operated to generate power continuously for approximately 4000 hours, thereupon it is taken off line for routine maintenance, inspection, and repair of any components identified during inspection. Taking a gas turbine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor is rotated in "turning gear mode" by an auxiliary drive motor at approximately 10 RPM or less, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector.

If a series of different images of different areas of interest within a given turbine inspection port are desired, the operator must manually re-position the camera inspection system bore scope to achieve the desired relative alignment of internal area of interest and the field of view. Relative alignment can be achieved by physically moving the bore scope so that its viewing port is positioned proximal a static area of interest. Examples of such relative movement of bore scope and static turbine component are by inserting a bore scope in different orientations within a static combustor or radially in and out of space between a vane and blade row within the turbine section. Relative alignment can also be achieved by maintaining the bore scope viewing port in a static position and moving the turbine internal component of interest into the static viewing field. An example of relative movement of turbine internal component and static bore scope is inspection of different blades within a blade row by manually rotating the turbine rotor sequentially a few degrees and capturing the image of a blade. The rotor is rotated sequentially to align each desired individual blade in the row within the camera viewing field.

Complete turbine inspection requires multiple manual relative repositioning sequences between the camera inspection system viewing port and areas of interest within the turbine by a human inspector. Inspection quality and productivity is subject to the inspection and manipulation skills of the inspector and inspection team. Inspection apparatus positioning is challenging due to the complex manipulation paths between components in a gas turbine. For example, insertion of a bore scope through a combustor inspection port in order to inspect the leading edge of first row vanes or related supports requires compound manipulations. Improper positioning of inspection apparatus within a turbine potentially can damage turbine internal components. Often an inspection team of multiple operators is needed to perform a manual inspection using known inspection methods and apparatus. In summary, known manual camera inspection procedures and inspection system manipulation are time consuming, repetitive in nature, and often require assistance of an inspection team of multiple personnel. The "human factor" required for known manual camera inspection procedures and inspection system manipulation introduces undesirable inspection process variances based on human skill level differences. Given human skill variances, some inspection teams are capable of completing inspections in less time, achieve better image quality and have lower inspection damage risk than other teams. Ideally skills of a high performing inspection team could be captured for use by all teams.

A need exists in the art for optical camera inspection systems and methods that reduce total time necessary to perform a nondestructive internal inspection of power generation machinery, including by way of non-limiting example steam or gas turbines and generators than is attainable by known inspection apparatus and methods, so that the machinery can be brought back on line for resuming power generation more quickly during maintenance cycles.

Another need exists in the art for optical camera inspection systems and methods that are capable of positioning inspection apparatus within power generation machinery, including by way of non-limiting example steam or gas turbines and generators, consistently and repetitively within an individual machine's inspection cycle or within inspection cycles of multiple different machines, with minimized risk of damage to machine internal components, high image quality and quicker inspection cycling time than is attained by the known manual inspection apparatus and methods.

Yet another need exists in the art for optical camera inspection systems and methods that help to equalize inspection skill level and productivity among different inspection teams.

SUMMARY OF THE INVENTION

Accordingly, potential objects of the present invention, jointly or severally among others, are to create optical camera inspection systems and methods for power generation machinery, (including by way of non-limiting example steam or gas turbines and generators) that compared to known inspection apparatus and methods: reduce total scheduled maintenance period time and individual inspection cycle time; position inspection apparatus consistently and repetitively within an individual machine's inspection cycle or within inspection cycles of multiple different machines, with minimized risk of damage to machine internal components and high image quality; and that help to equalize inspection skill level and productivity among different inspection teams.

Internal components of power generation machinery, such as gas and steam turbines or generators, are inspected with an optical camera inspection system that is capable of automatically positioning the camera field of view (FOV) to an area of interest within the machinery along a pre-designated navigation path and capturing images without human intervention. Automatic camera positioning and image capture can be initiated automatically or after receipt of operator permission. The pre-designated navigation path can be defined by operator manual positioning of an inspection scope within the power machine or a similar one of the same type, and recording the sequence of positioning steps for future replication. The navigation path can also be defined by virtual simulation.

These and other objects are achieved in accordance with the present invention by a system for internal inspection of power generation machinery, including generators and industrial gas or steam turbines. The system includes a base for affixation to a power generation machine inspection port. An inspection scope having a proximal end is coupled to the base, and has at least one degree of motion that is capable of remote control and actuation by a control system. A camera, having a field of view, is coupled to the inspection scope distal the base, and is capable of remote control and image capture by a control system. The system also has a control system coupled to the inspection scope and camera, for automatically positioning the inspection scope and camera field of view along a pre-designated navigation path within a power generation machine to an internal area of interest and for capturing a camera image thereof without human intervention.

The present invention also features a method for internal inspection of power generation machinery, and includes the steps of providing an internal inspection system. The inspection system has a base for affixation to a power generation machine inspection port. An inspection scope has a proximal end coupled to the base, and at least one degree of motion that is capable of remote control and actuation by a control system. A camera, having a field of view, is coupled to the inspection scope distal the base. The camera is capable of remote control and image capture by a control system. The system also has a control system coupled to the inspection scope and camera, for automatically positioning the inspection scope and camera field of view along a pre-designated navigation path within a power generation machine of the type being inspected to an internal area of interest and for capturing a camera image thereof without human intervention. The method further includes the steps of affixing the base to a power machine inspection port and providing the navigation path to the control system. Next, the power machine is inspected by automatically positioning the inspection scope and camera field of view along the navigation path with the control system and capturing a camera image thereof without human intervention. The order of steps may be modified when performing this method.

The present invention also features a method for inspecting an industrial gas turbine. First, the gas turbine is shut down to cease power generation operation. An internal inspection system is provided that has a base for affixation to an inspection port of the turbine. An inspection scope is provided that has a proximal end coupled to the base, and at least one degree of motion that is capable of remote control and actuation by a control system. A camera, having a field of view, is coupled to the inspection scope distal the base. The camera is capable of remote control and image capture by a control system. The inspection system includes a control system coupled to the inspection scope and camera, for automatically positioning the inspection scope and camera field of view along a pre-designated navigation path within the gas turbine to an internal area of interest and for capturing a camera image thereof without human intervention. The gas turbine is cooled to an internal temperature of less than 150° C. (300° F.) and the base is affixed to an inspection port of the gas turbine. A navigation path is provided to the control system. Thereafter the gas turbine is inspected by automatically positioning the inspection scope and camera field of view along the navigation path with the control system and capturing a camera image thereof without human intervention. The camera image or plurality of images is stored for review. The order of steps may be modified when performing this method.

The navigation path is pre-determined by a number of methods and subsequently recorded for future replication by the control system of the actual inspection scope used in the inspecting step. The navigation path pre-determination methods may include: prior human controlled positioning of an inspection scope of the type used in the inspecting step within the actual inspected gas turbine (or within another gas turbine having the same type of internal structure as the actual inspected gas turbine) along a selected navigation path; human controlled simulated positioning of a virtual inspection scope of the type used in the inspecting step within a virtual power generation machine of the type being inspected along a selected navigation path; and simulated positioning of a virtual inspection scope and virtual power generation machine of the type used in the inspecting step along a simulated selected navigation path without human intervention.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which:

FIG. 10 is a schematic elevational view of a camera head articulation and rotation (pan) mechanism of the optical camera inspection system of FIG. 5, showing the Φ and θ degrees of motion;

FIG. 11 is a schematic plan view of a camera head articulation and rotation (pan) mechanism of FIG. 10;

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in optical camera systems for nondestructive internal inspection of power generation machinery, including by way of non-limiting example steam or gas turbines and generators. The optical camera inspection system is capable of automatically positioning the camera field of view (FOV) to an area of interest within the machinery and capturing images without human intervention. Automatic camera positioning and image capture can be initiated automatically or after receipt of operator permission. Alternatively, the system may be human-operated in "manual" mode.

Camera Inspection System Overview

Figure 1:
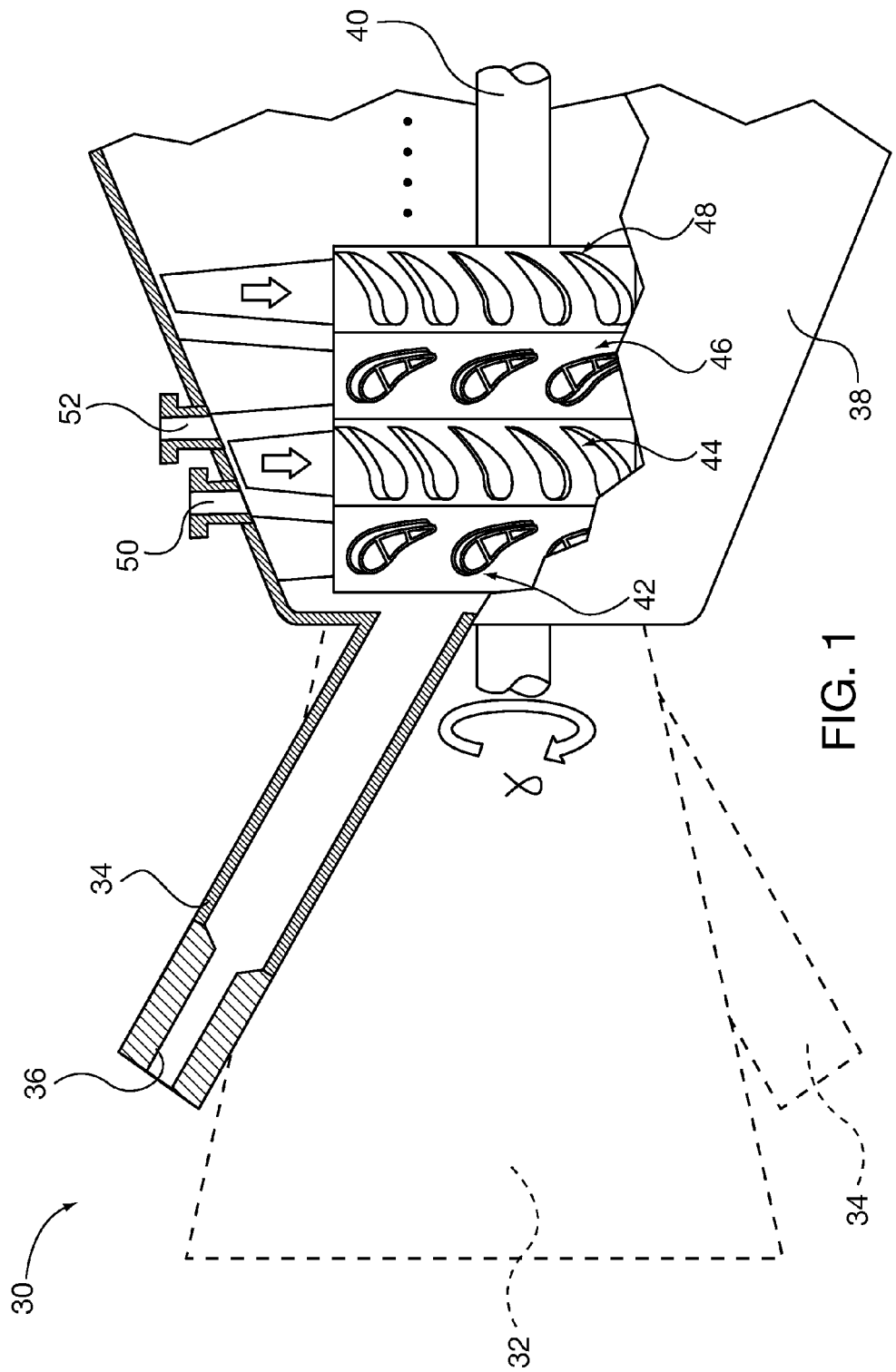
FIG. 1 is a partial cross sectional schematic view of a known gas turbine.

Referring to FIG. 1, embodiments of the present invention facilitate automated off-line remote visual inspection of gas turbine 30 internal components, including combustors 34; turbine section Row 1 and Row 2 fixed vanes 42, 46; leading Row 1 and Row 2 rotating blades 44, 48; and ring segments. As shown in FIGS. 2-4 and 18, embodiments of the present invention inspection system enables inspection of offline turbines that have not fully cooled to ambient temperature by attaching remote-actuated optical camera inspection scope probes 60, 220 to turbine inspection ports 36, 50 and 52. Upon attachment the inspection scope probes 60, 220 are selectively positioned (manually by an operator or automatically without an operator) via internal motion control servo motors that are under command of a motion control system. Image data are acquired, captured, and if desired archived for further analysis.

Articulated Inspection Scope

Figure 2:
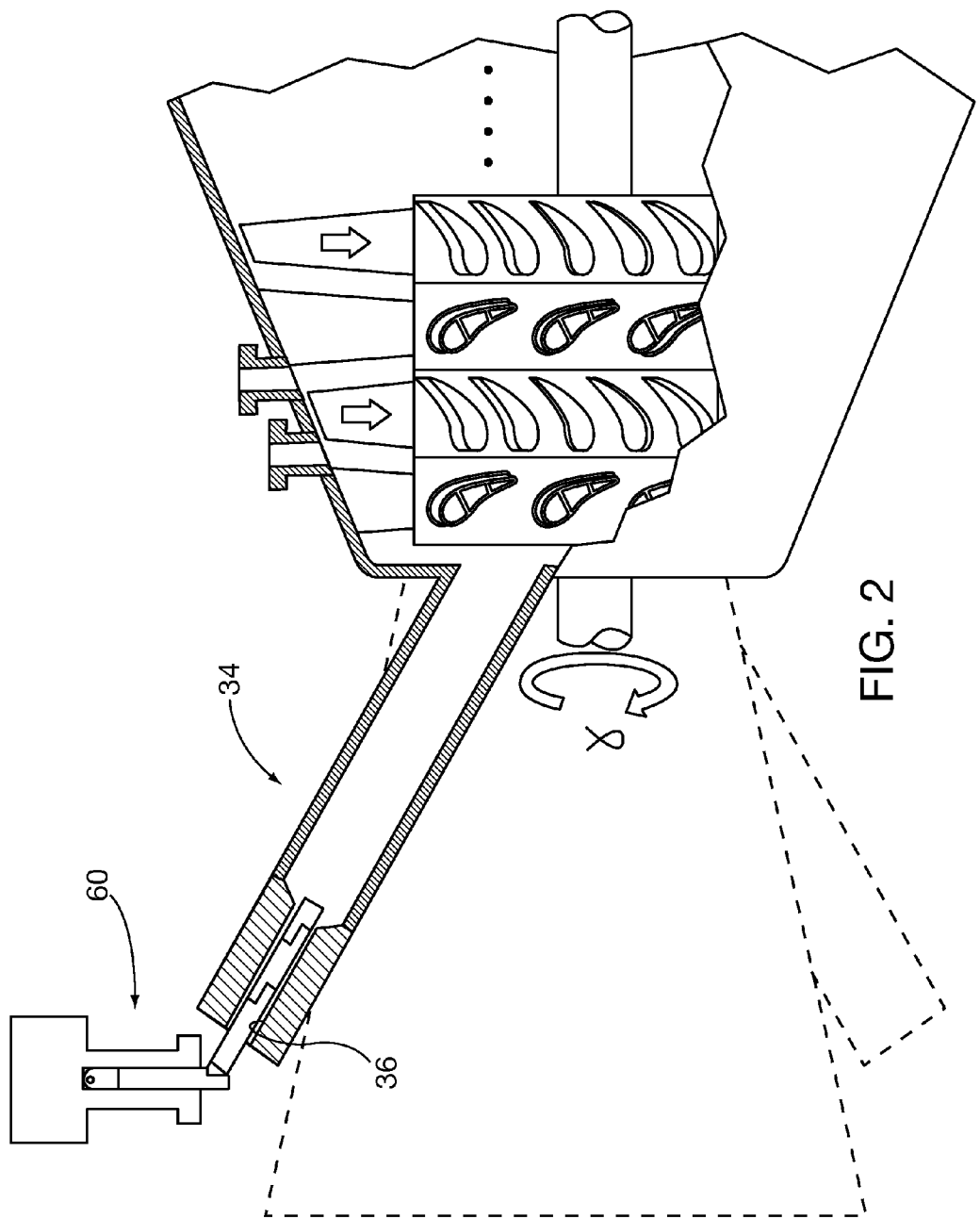
FIG. 2 is a partial cross sectional schematic view of a known gas turbine showing partial insertion of an optical camera inspection system embodiment of the present invention into a combustor inspection port.
Figure 3:
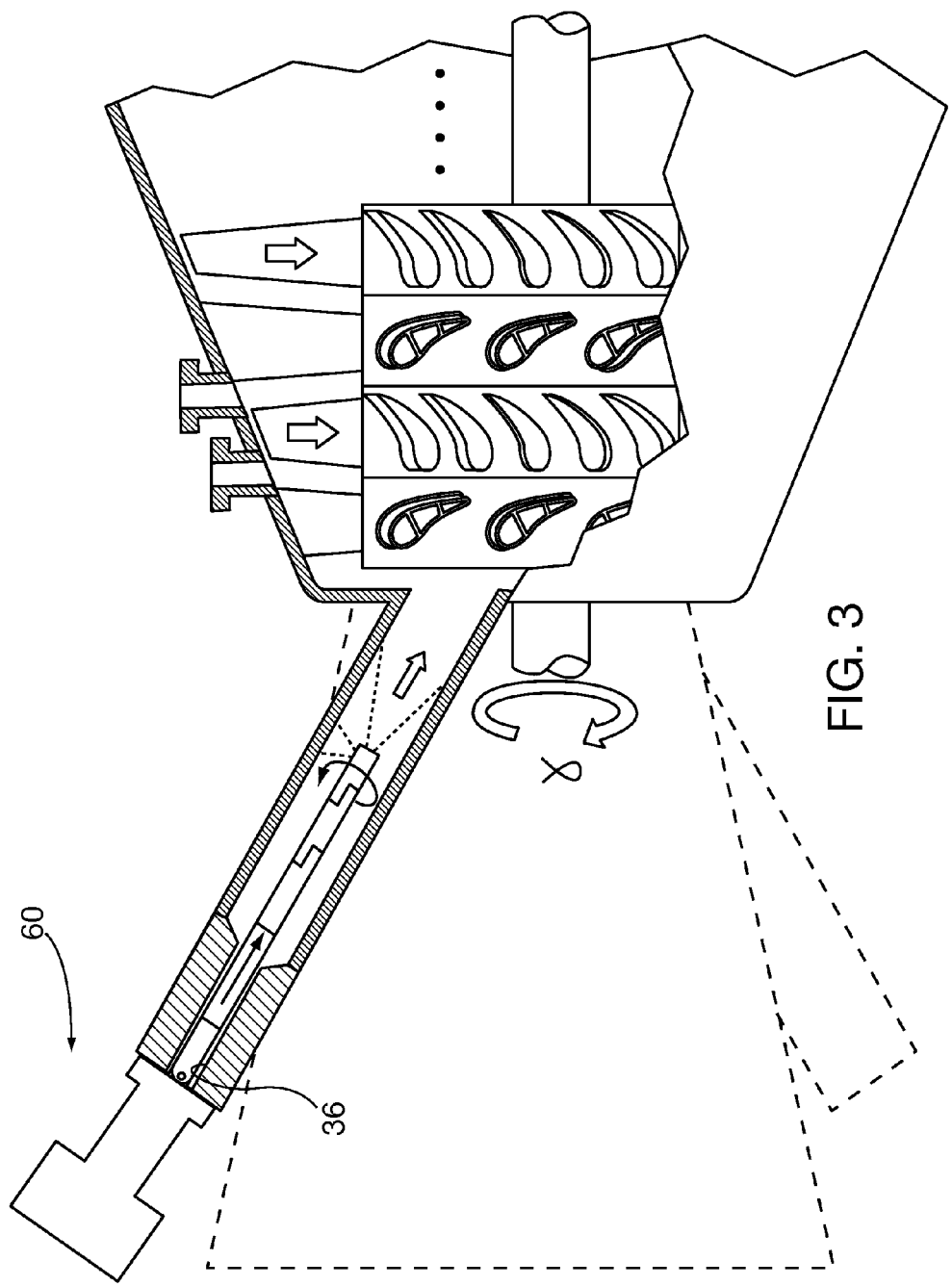
FIG. 3 is partial cross sectional schematic view of a known gas turbine performing an inspection of a combustor internal components with the optical camera inspection system of FIG. 2.
Figure 4:
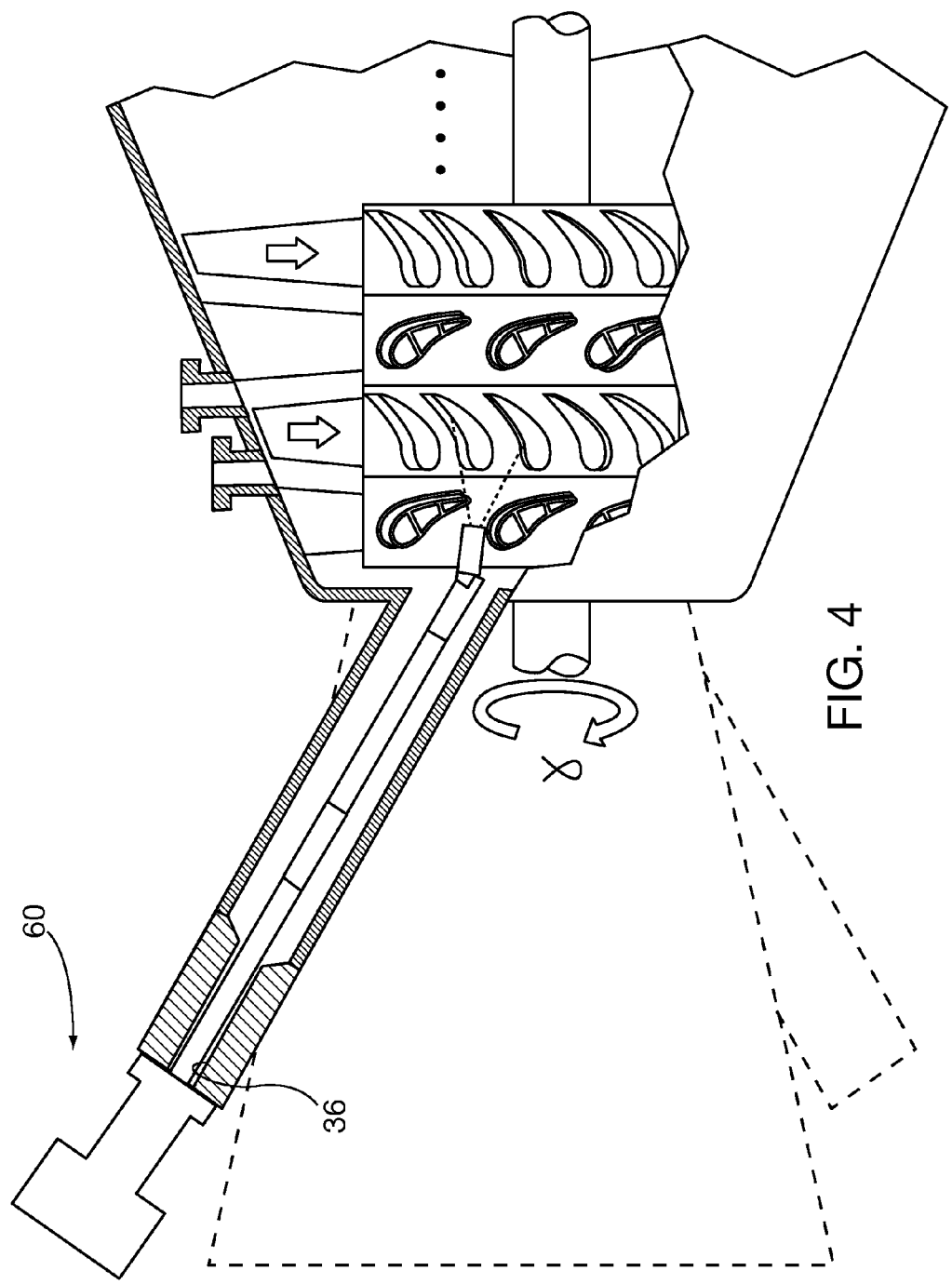
FIG. 4 is partial cross sectional schematic view of a known gas turbine performing an inspection of the leading edge of row 1 turbine blades with the optical camera inspection system of FIG. 2.

FIGS. 2-4 show inspection of a gas turbine by insertion (FIG. 2) of an articulated inspection scope embodiment 60 into a combustor 34 inspection port 36. For maneuvering clearance of the scope 60 about the confines of a gas turbine installation, inspection scope 60 has a folding knuckle, so that the scope can be folded into a generally L-shape profile about half as long as an elongated scope. Once the scope 60 is positioned within the inspection port 36, the knuckle is straightened, as shown in FIG. 3. After the inspection scope 60 is affixed to the inspection port 36 it may be utilized to inspect to combustor internal components by rotating and extending its camera head. In FIG. 4, as the scope 60 is further extended and its camera head articulated images of the Row 1 vanes and leading edge of Row 1 blades may be acquired. If the turbine rotor is in turning mode, images of all Row 1 blades may be captured as they rotate past the camera head field of view.

Figure 5:
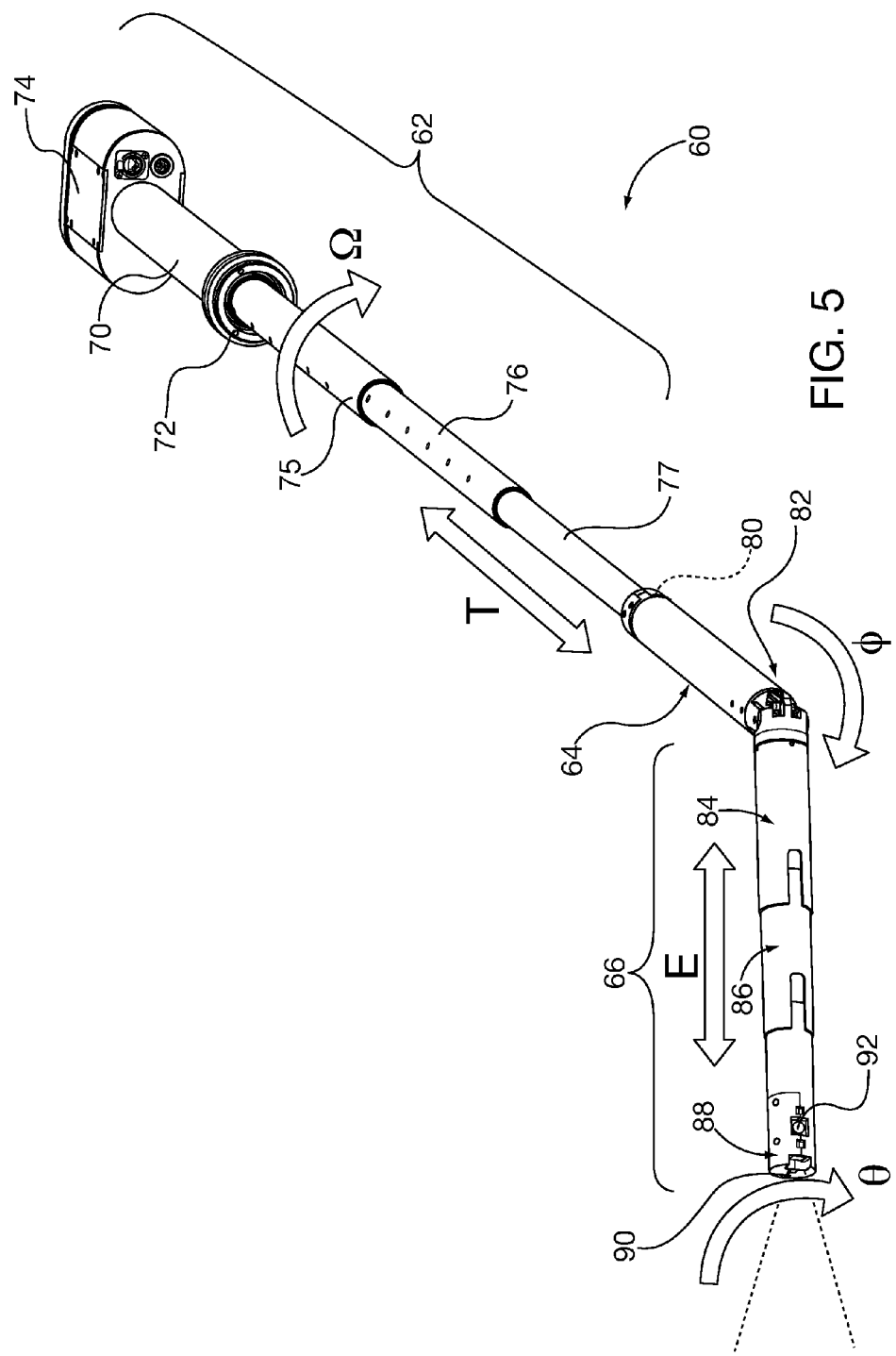
FIG. 5 is a perspective schematic view of the optical camera inspection system of the embodiment of FIG. 2, showing available degrees of motion Ω, T, Φ, E and θ.

Referring to FIG. 5, the inspection scope 60 has three main component sections: extension tube section 62 (see FIGS. 5-9); motor can 64 (FIGS. 5, 10-12); and camera tip 66 (FIGS. 5, 12-15) that are capable of performing the following five degrees of motion freedom:

Ω—gross rotation;
T—telescoping extension;
Φ—camera head articulation;
E—camera head tip extension; and
θ—camera head rotate/pan.

The extension tube section 52 has a mounting tube 70 and mounting collar 72 that are attached to an inspection port, such as the combustor inspection port 36. Motor housing 74 is attached to the opposite end of mounting tube 70 distal the mounting collar 72 and houses the servo motors necessary to perform the Ω and T degrees of motion. Three telescoping tubes 75-77 collapse into the mounting tube 70 for providing the T directional motion.

Figure 6:
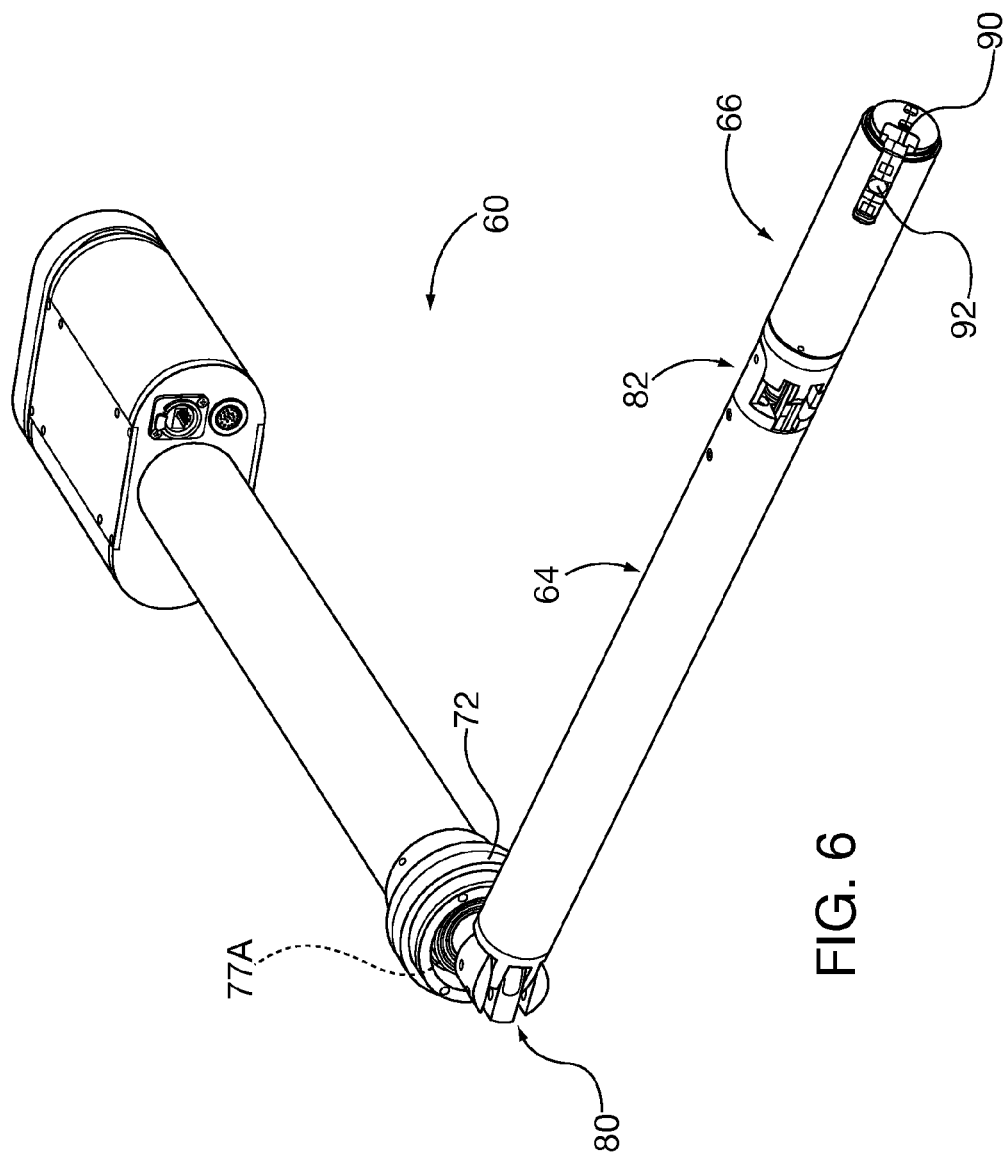
FIG. 6 is a perspective schematic view of the optical camera inspection system of FIG. 5, in the folded insertion position of FIG. 2.
Figure 7:
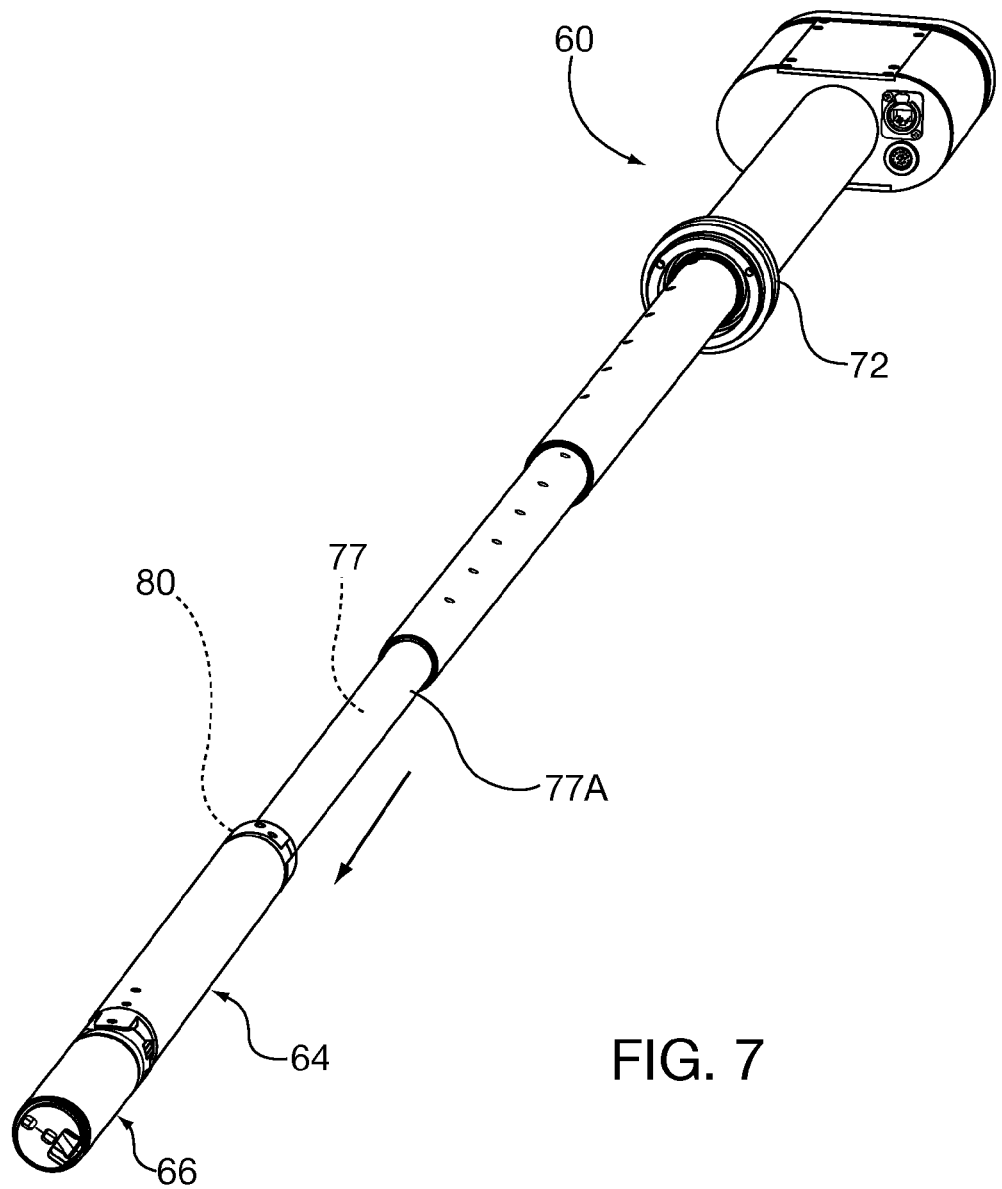
FIG. 7 is a perspective schematic view of the optical camera inspection system of FIG. 5, in the locked inspection position of FIG. 3.

As shown in FIGS. 6 and 7, spring loaded locking knuckle 80 enables the entire inspection scope 60 to fold for compact maneuvering about the turbine 30, as shown in FIG. 2 and described above. Locking sleeve 77A slides over telescoping tube 77 and restrains knuckle 80 therein when the inspection scope 60 is in is locked inspection position as shown in FIG. 7.

As shown in FIG. 5, motor can 64 houses the servo motors necessary to position motorized articulating joint 82 that provides the Φ degree of motion, the camera head 66 head extension motion E via the camera head telescoping extensions 84, 86 and the camera head 88 rotate/pan degree of motion θ. The camera head 88 includes camera ports 90, 92 for respective axial and lateral fields of view (FOV).

Figure 8:
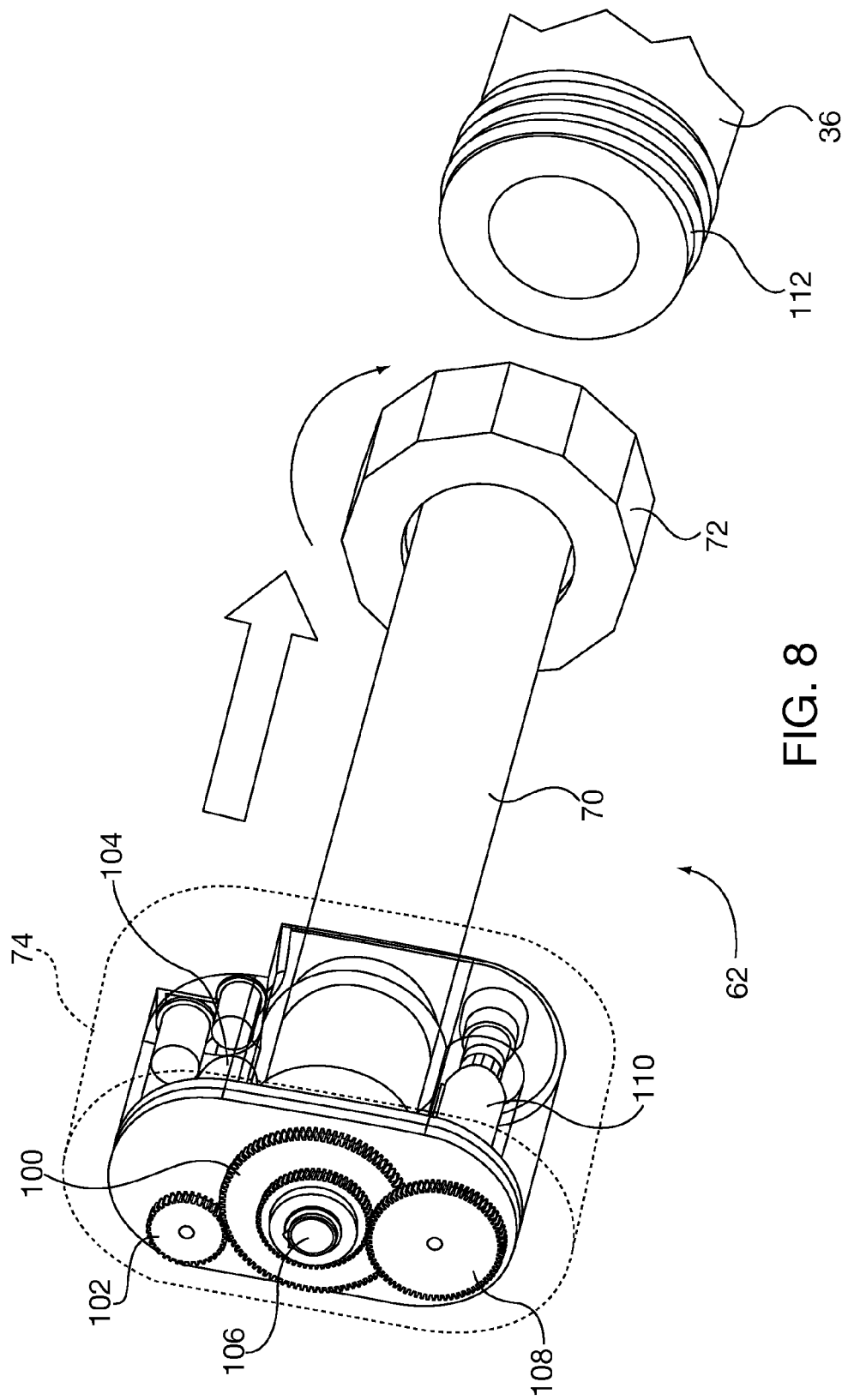
FIG. 8 is a perspective schematic view of the extension tube mechanism portion of the optical camera inspection system of FIG. 5, showing the Ω and T degrees of motion.
Figure 9:
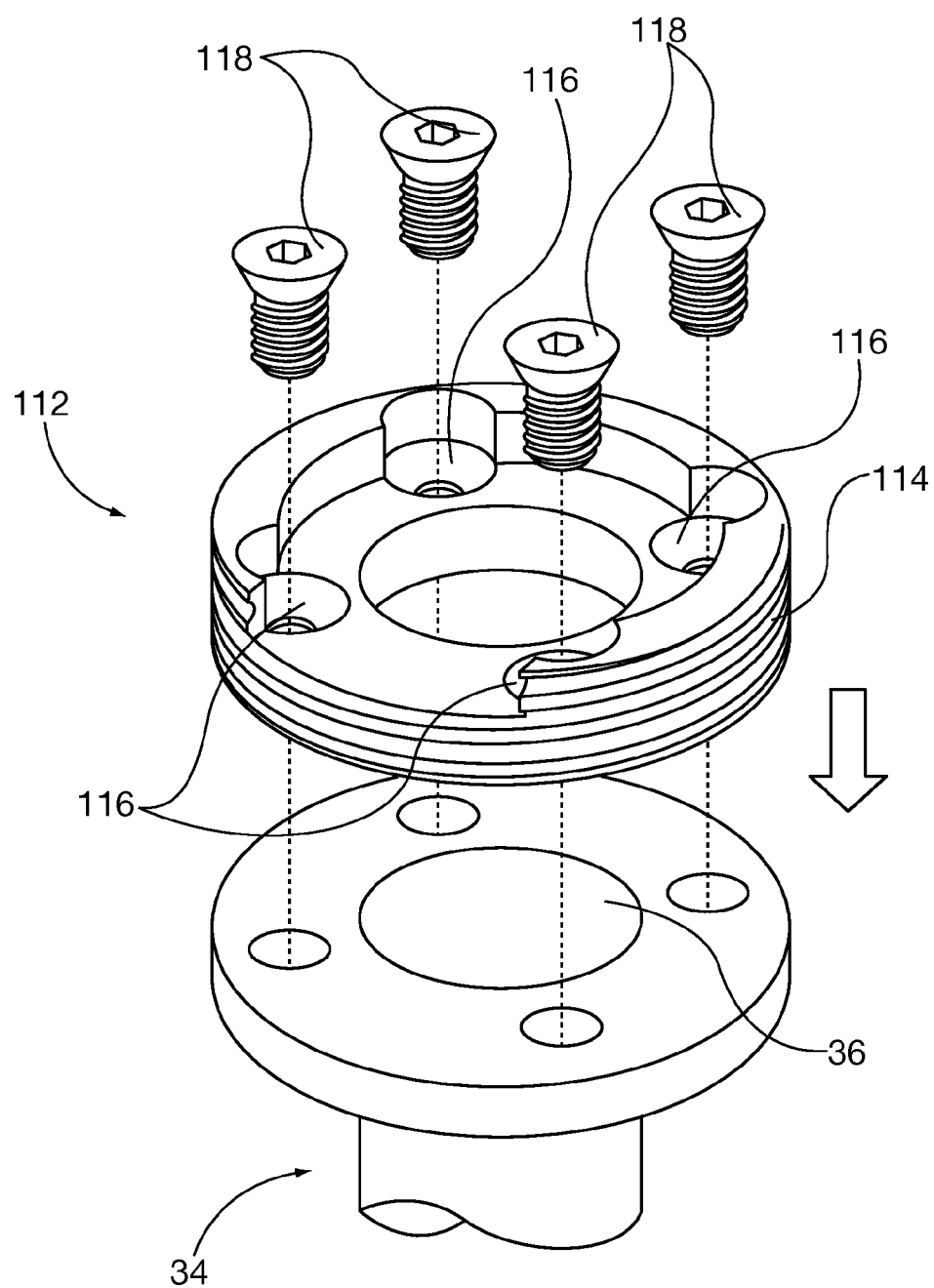
FIG. 9 is a schematic perspective view of an adapter ring of the present invention being attached to a turbine inspection port.
Figure 12:
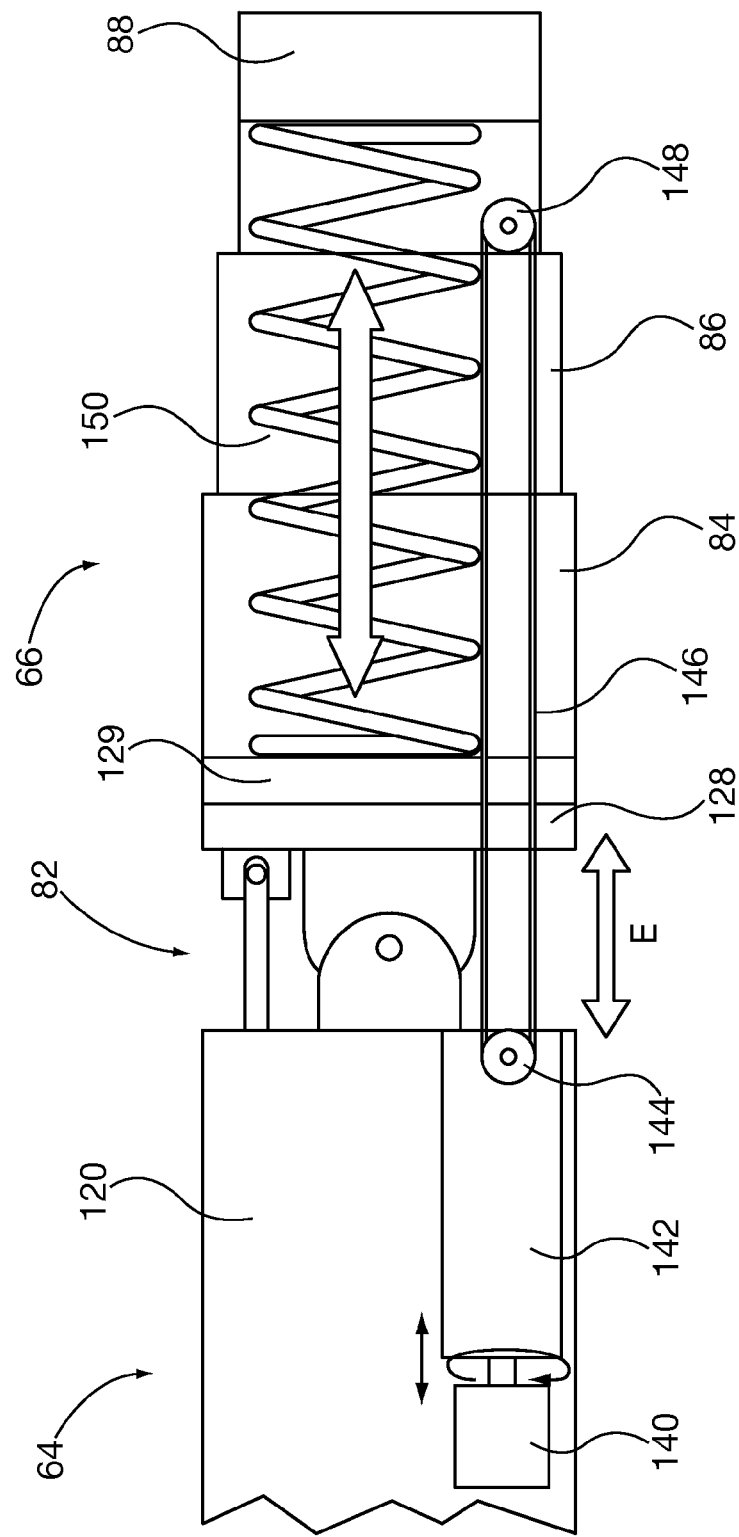
FIG. 12 is a schematic elevational view of a camera head extension mechanism of the optical camera inspection system of FIG. 5, showing the E degree of motion.

FIG. 8 is a detailed view of the motor housing 74, showing two coaxially nested, independently driven large and small diameter gears in the rotation hub 100. Rotate drive gear 102 is driven by the rotate servo motor 104, for effectuating the Ω motion by rotating the larger diameter gear in the rotation hub 100. Telescope extension drive screw 106 is rigidly coupled to the smaller diameter gear in rotation hub 100, that in turn engages the extend drive gear 108. Extend servo motor 110 is responsible for effectuating the T motion by rotating the smaller diameter in the rotating hub 100. Mounting collar 72 attaches to adapter ring 112, that is in turn attached to an inspection port, such as the combustor inspection port 36. As shown in FIG. 9, the adapter ring includes a plurality of peripheral threads 114 that are engaged with mating internal threads within the collar 72. The adapter ring 112 has mounting holes 116 for receipt of tapered head machine screws 118. The screws 118 may be captively mounted within adapter ring 112. Other configurations of adapter ring or other forms of base that affixes the scope to an inspection port may be substituted for the adapter ring 112.

Referring to FIG. 10, motor can 64 has a motor can housing 120 with a pair of spaced apart ear-like motor can pivots 122. Articulate motion servo motor 124 rotates drive screw 126 that imparts the Φ articulating motion by tipping camera pivoting hub 128. The tipping motion axis 132 is established between camera hub pivot 130 that is rotatively coupled to the motor can pivot 122. Offset link 133 is coupled to drive screw 126 and converts linear motion to rotational motion about tipping motion axis 132.

Motor can housing 120 also contains camera pan/rotate servo motor 134 that imparts the θ degree of motion on camera head 66, as shown in FIG. 11. Servo motor 134 drives bevel gear train 136, which in turn includes the driven bevel gear that is rotatively captured within camera pivoting hub 128, for in turn rotating the rotating hub 129. The rotating hub 129 is rigidly coupled to the camera head telescoping extension 84. Camera tip telescoping extensions 84 and 86 are extended and retracted in the E motion degree by extension servo motor 140, that in turn engages linear drive screw 142. The drive screw 142 includes drive pulley 144, over which passes tensioned cable 146. Slave pulley 148 is attached to camera head 88 and is also coupled to cable 146. Coil spring 150 is interposed between camera head 88 and rotating hub 129, and biases them away from each other, thereby tensioning cable 146. It follows that selective translation of the drive screw 142 by the extension servo motor 140 moves the camera head 88 to the left and right in the figure (motion E).

Figure 13:
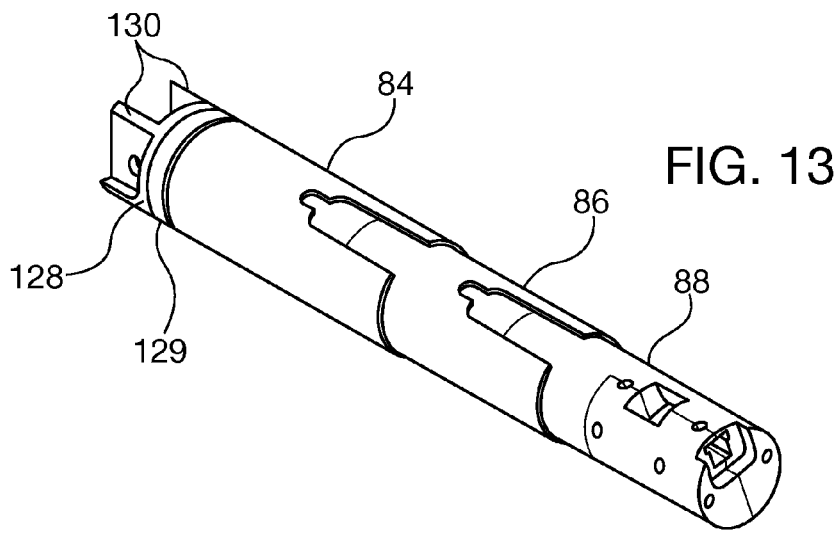
FIG. 13 is a schematic perspective view of the camera head of the optical camera inspection system of FIG. 5.
Figure 14:
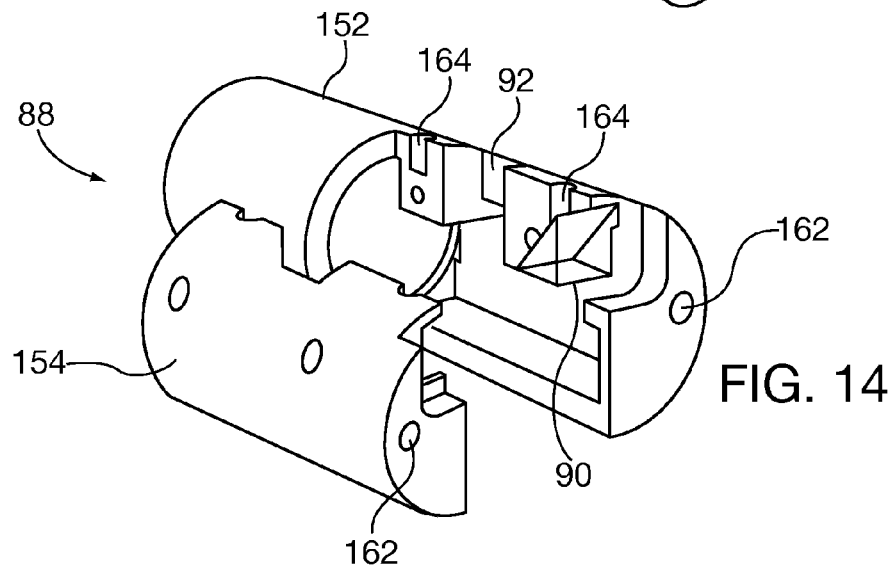
FIG. 14 is a schematic exploded perspective view of a camera head of the optical camera inspection system of FIG. 5.
Figure 15:
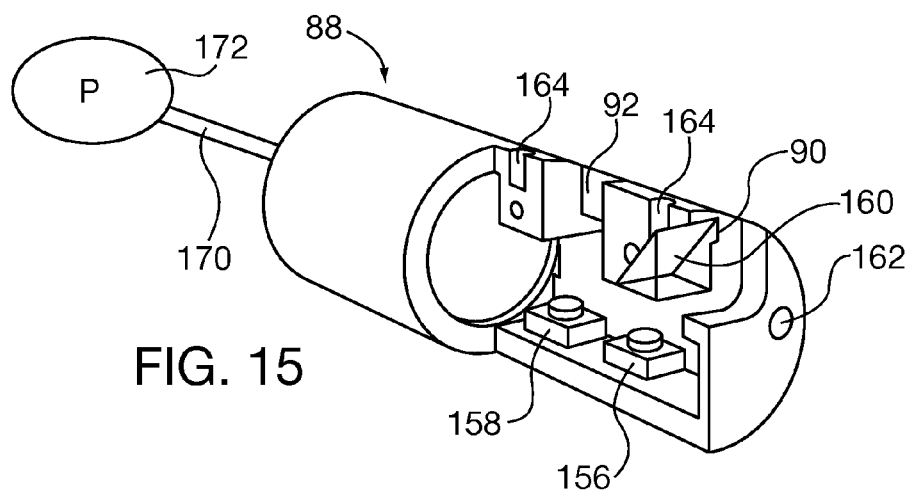
FIG. 15 is a schematic partial assembly perspective view of the camera head of FIG. 14.

FIGS. 13-15 show the camera head 88 that has a clamshell construction with camera head housing 152 and selectively removable cover 15. Camera 156 has a field of view (FOV) through "camera 1" port 90, extending along the central axis of the camera head 88. Camera 158 has a field of view (FOV) through "camera 2" port 92, extending laterally or normal to the central axis of the camera head 88. Camera 156 generates its image through prism 160. Cameras 156, 158 are known auto-focusing USB cameras of the type routinely used with personal computers. Light emitting diodes (LEDs) 162 and 164 provide illumination for the cameras 156, 158 during internal inspection of power generation machinery.

Inspection scope 60 is externally cooled by a cooling air line 170 and pressurized cooling air source 172 (e.g., compressed air), schematically shown in FIG. 15. Cooling air passes through the scope 60 to transfer heat away from the instrument, where it exhausts through gaps within the scope outer surface, such as the camera ports 90, 92, the prism 160, around the cameras 156, 158 and the LEDs 162, 164. Those gaps effectively function as cooling air exhaust ports. Cooling air exhausting the various cooling ports helps transfer heat out of the scope 60 and helps create a thermal barrier around the camera head 88 that is relatively cooler than the not fully cooled turbine 30 internal temperature. In this manner the inspection scope 60 can be inserted into still hot shut-down turbine many hours before it cools to ambient air temperature. In this manner inspection can be initiated many hours—and possibly days—earlier than was permissible with known inspection systems. In this manner an inspection process can be initiated and completed earlier in a turbine service period than was possible in the past, possibly reducing the aggregate maintenance cycle time.

Camera Inspection Scope Control and Operation

Figure 16:
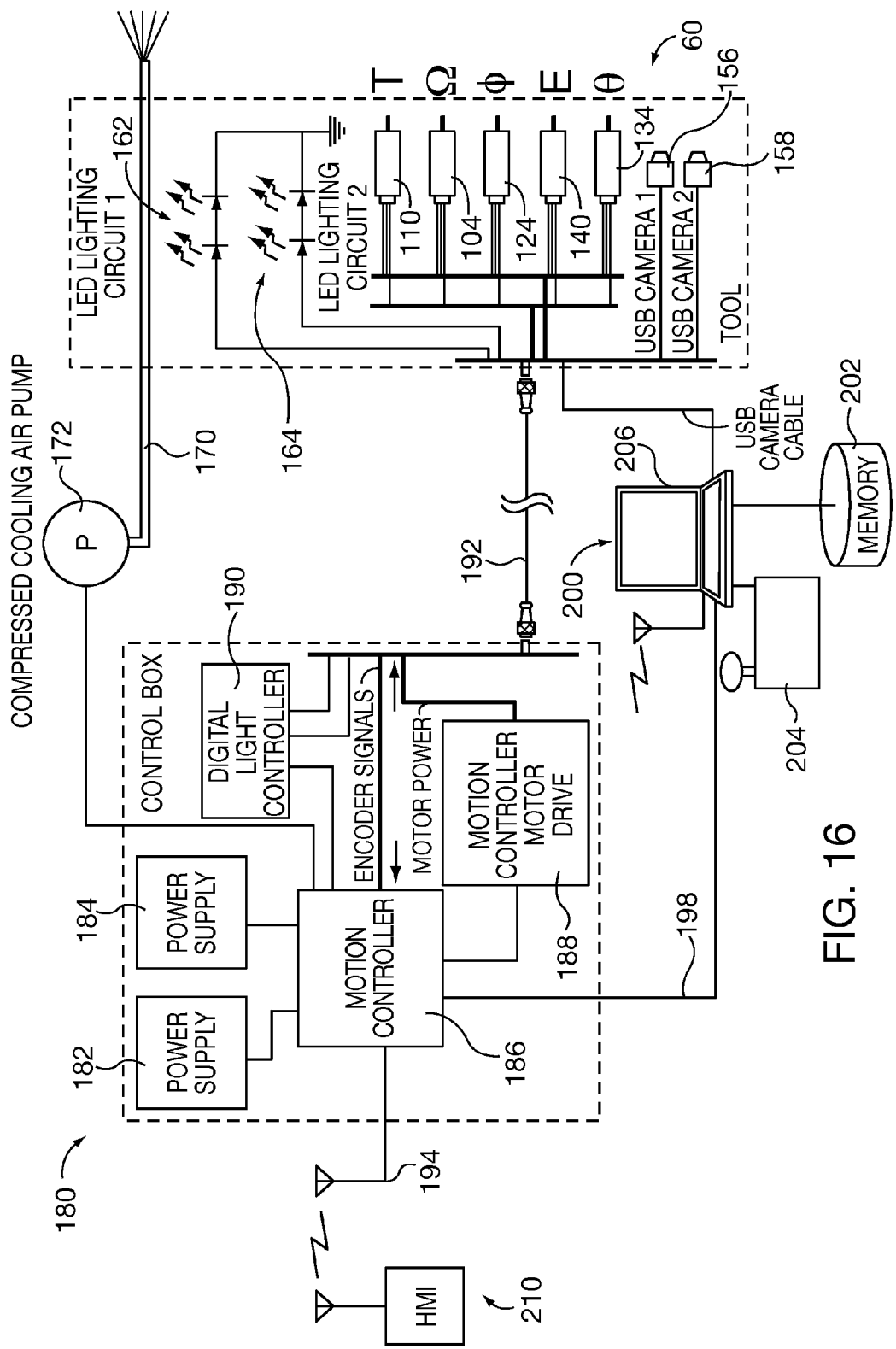
FIG. 16 is a block diagram of the control box and controls system for the optical camera inspection system of FIG. 5.

Inspection scope 60 positioning along its five degrees of motion are accomplished by energizing the five previously described precision motion control servo motors 104 (Ω), 110 (T), 124 (θ), 124 (Φ), and 140 (E). The servo motors have associated encoders that provide motor position information feedback for use by the controller of a known motion control system. FIG. 16 is block diagram of an exemplary motion control system of the present invention. The previously described inspection scope 60 hardware is designated by dashed line 60, and is in communication with control box 180, also designated by dashed line, by way of known communication pathways, such as multi-pathway cable 192 and a USB camera cable.

Control box 180 includes first and second power supplies 182, 184 for powering motion controller 186 and motion controller motor drive 188. All of components 182-188 are of known design utilized for industrial motion control systems. The motion controller 186 issues commands to the motion controller motor drive 188 for energizing and reversing the inspection scope 60 servo motors 104 (Ω), 110 (T), 124 (θ), 124 (Φ), and 140 (E). For brevity all such motors are collectively referred to as "servo motors". The respective servo motors have associated encoders that generate encoder signals indicative of the scope position within its respective range of motion. For example, the encoder associated with servo motor 104 generates a rotational position signal indicative of the gross rotational position (Ω) of the extension tube portion 62. Position signal information from each encoder is accessed by the motion controller 186. The motion controller 186 correlates respective motor encoder signals with inspection scope 60 spatial position. Digital light controller 190 controls the LED 162, 164 luminal output and on/off, and communicates with the motion controller 186. The motion controller 186 also controls cooling air flow into and through the inspection scope 60, for example flow rate out the cooling port 174.

Figure 17:
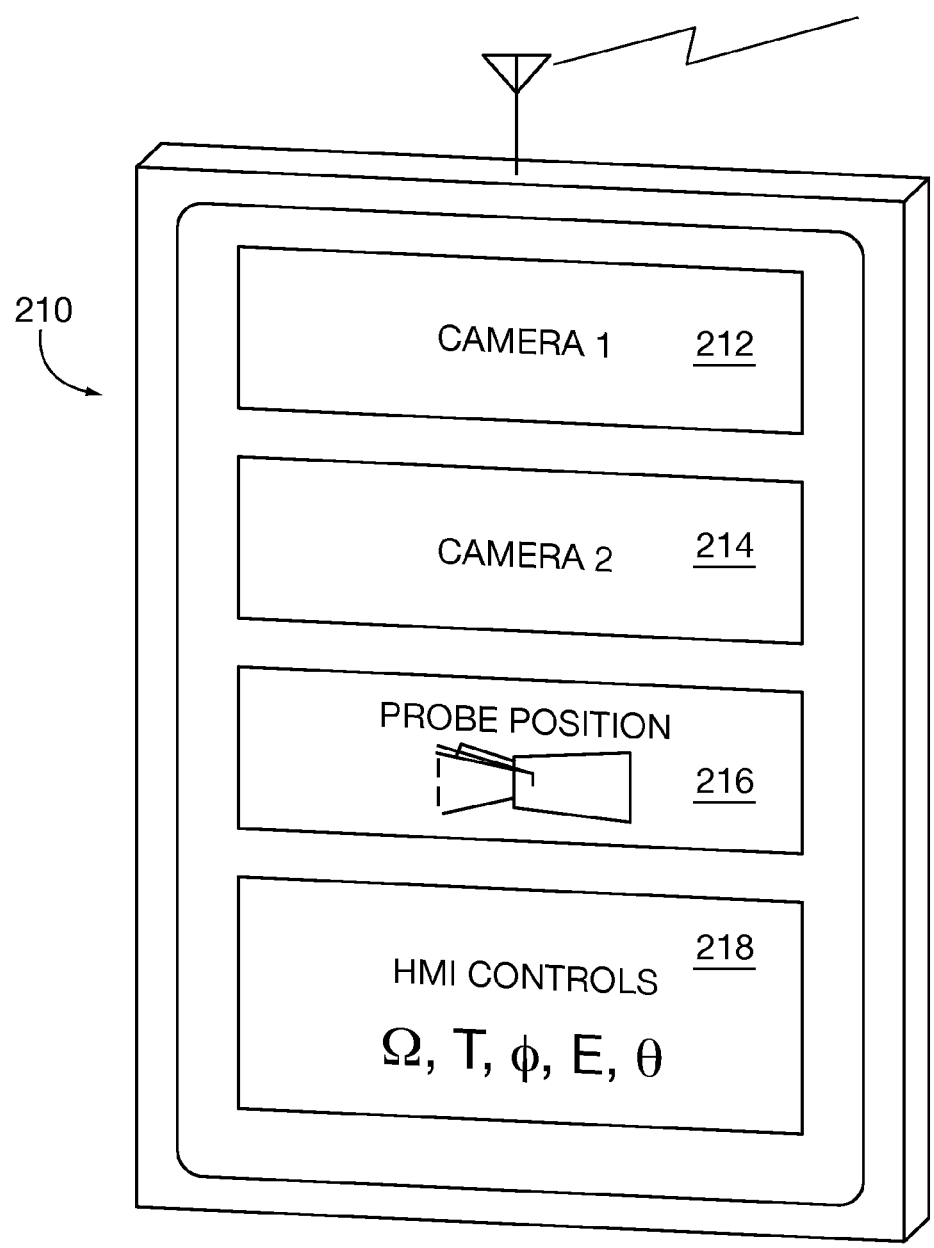
FIG. 17 is a perspective schematic view of an embodiment of a tablet computer human machine interface (HMI) for operator remote monitoring and control of the optical camera inspection system of the present invention.

Motion controller 186 has an optional wireless communication capability 194. Hardwired data pathway 198, for example a cable transmitting communications signals in conformity with Ethernet protocol, is in communication with a host controller 200. An exemplary host controller 200 is a personal computer with internal memory capacity and if desired external memory 202. The host controller computer 200 also receives and processes image data from camera 156 (USB Camera 1) and from camera 158 (USB Camera 2), that may be processed. The computer 200 may archive or otherwise store raw or processed image data in memory 202. Inspection scope 60 can be positioned under human command and control, such as via joystick 204 and/or HMI viewing/touch screen 206. Images from the cameras 156, 158 can be viewed by HMI viewing screen 206. Optionally the computer 200 may have wireless communication capability, for example to communicate with other computers, including for example a tablet computer 210 with HMI, such as for example a tablet computer. FIG. 17 shows an exemplary tablet computer HMI display screen including Camera 1 image display 212, Camera 2 image display 214, probe position information display 216 and an HMI control interface 218 for manipulating inspection scope 60 position. The tablet computer 210 may have direct communications capability with the motion controller 186, without the need to communicate through the host controller computer 200.

Blade/Vane Inspection Scope

Figure 18:
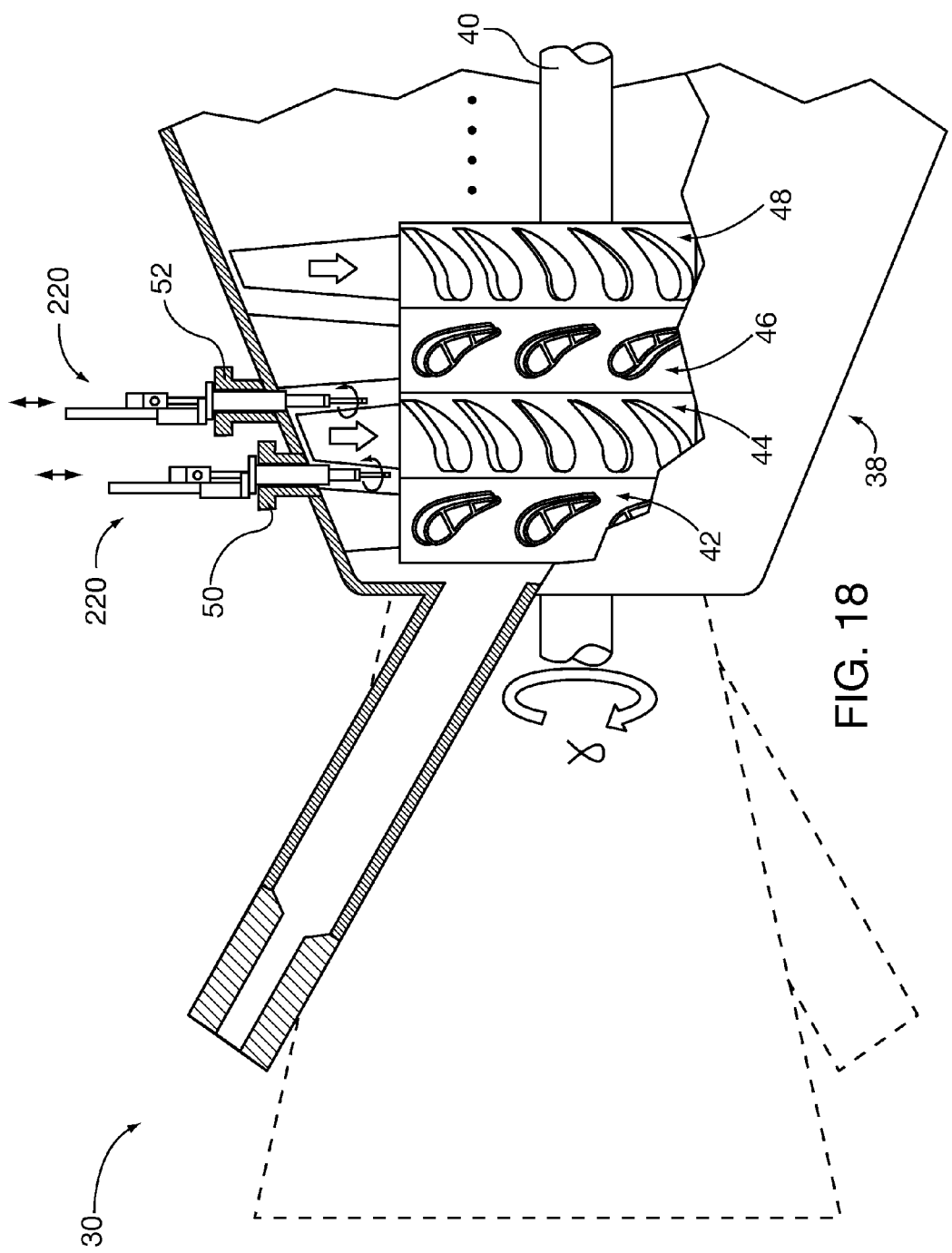
FIG. 18 is a partial cross sectional schematic view of a known gas turbine showing insertion of another optical camera inspection system embodiment of the present invention into two separate turbine section rows respective inspection ports.
Figure 19:
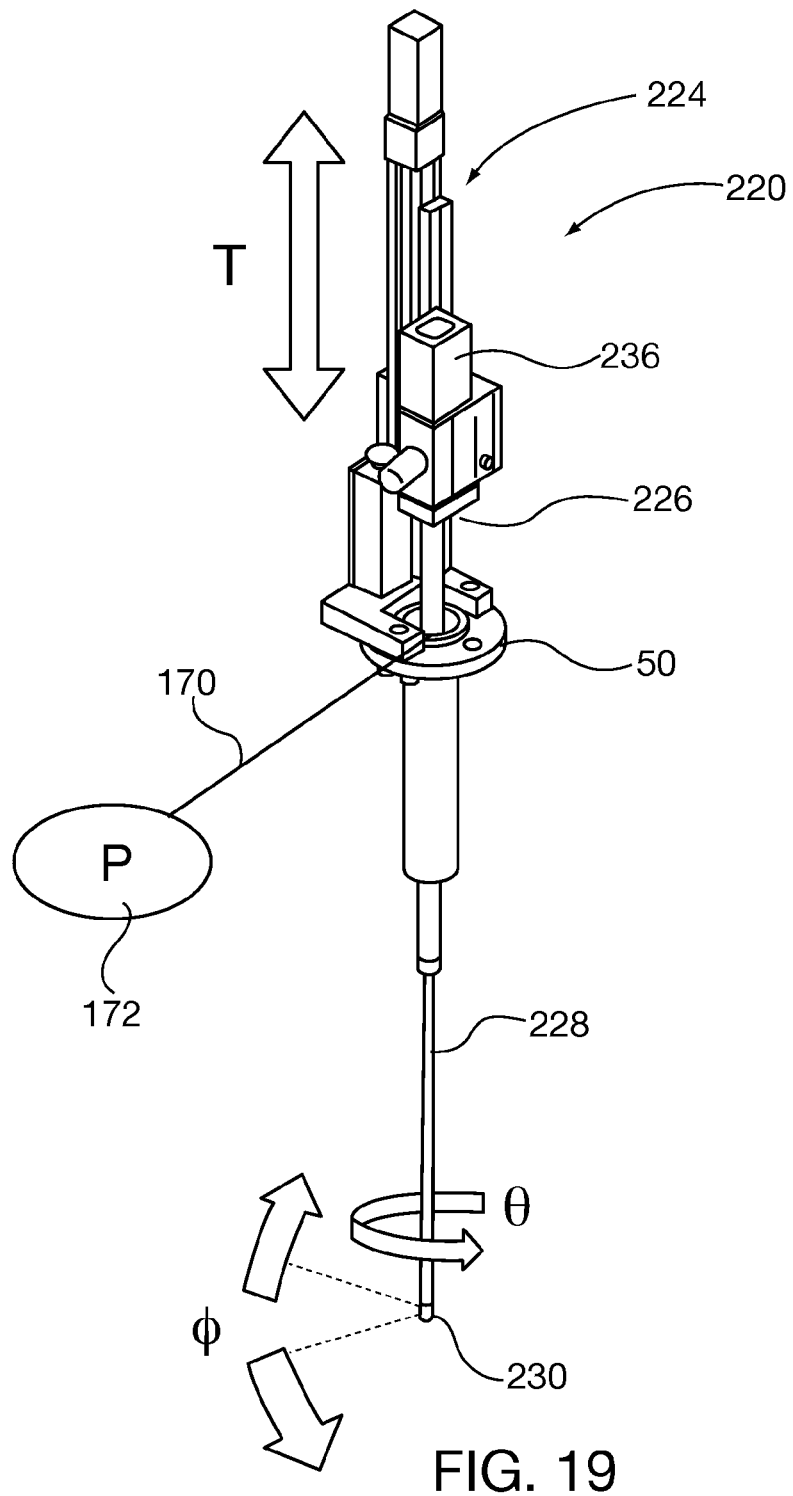
FIG. 19 is an elevational perspective view of optical camera inspection system embodiment of FIG. 18, showing available degrees of motion T, θ and Φ.
Figure 20:
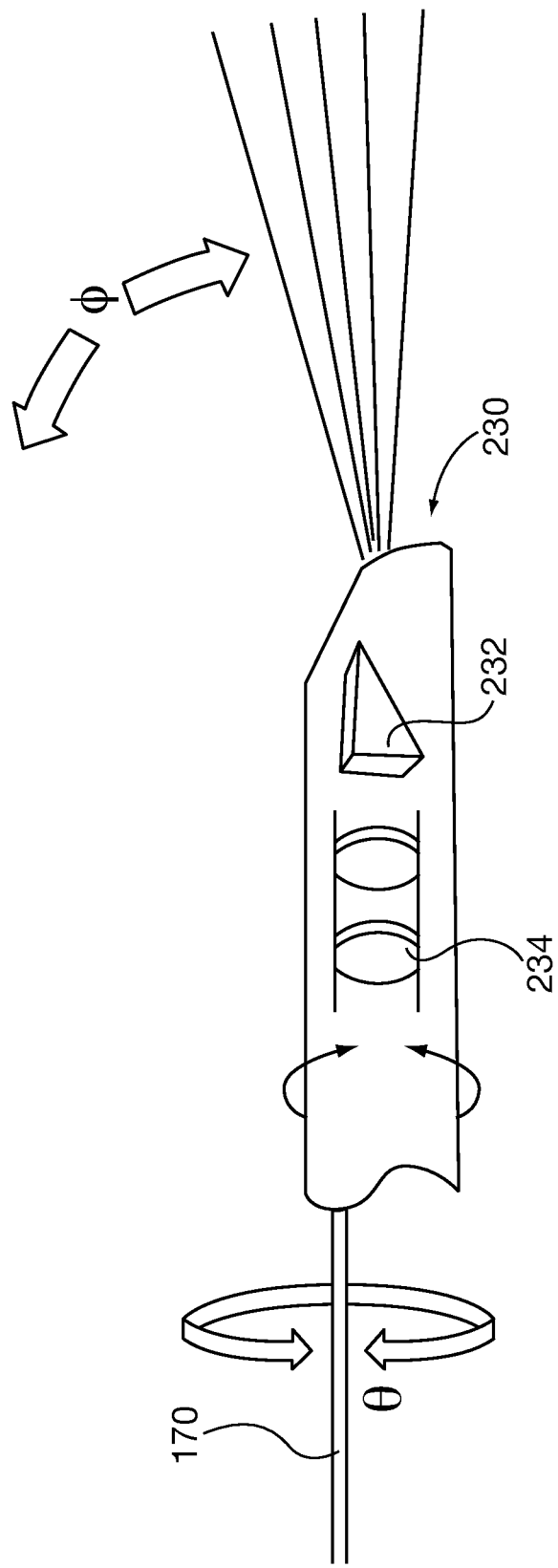
FIG. 20 is an elevational view of the swing prism articulation mechanism for the Φ degree of motion.

A blade/vane inspection scope 220 embodiment is shown in FIGS. 18-20. This embodiment is particularly suitable for inspection within the confines of a gas turbine 30 turbine section 38, between rows of rotating blades and stationary vanes. FIG. 18 shows a pair of inspection scopes 220 respectively mounted to each of the Row 1 inspection port 50 and Row 2 inspection port 52. However, at the discretion of an inspection team a single inspection scope 220 may be mounted to a selected inspection port or more than two inspection scopes 220 may be mounted to the turbine 30 simultaneously during an inspection procedure. Similarly, an inspection team at its discretion may also operate one or more of the inspection scope 60 embodiments simultaneously with or without the inspection scope 220 embodiment in any inspection procedure.

As shown in FIGS. 19 and 20 the inspection scope 220 embodiment is mounted to a gas turbine inspection port (here a Row 1 inspection port 50) by mounting flange 222. Linear drive 224 with an associated servo motor and encoder translates the inspection scope in the telescoping extension position motion degree T. Rotational drive 226 with an associated servo motor and encoder rotates the inspection scope in the camera rotate/pan motion degree $\theta$. Bore scope 228 is mechanically coupled to the linear drive 224 and rotational drive 226, and has a camera head 230 that captures within its field of view (FOV). The camera head 230 includes a pivoting prism 232 whose motion in the articulation $\Phi$ motion degree is imparted by an associated servo motor and encoder. The bore scope 228 is of known construction and includes fiber optic lenses 234 and auxiliary external lighting (not shown) that illuminate and transmit images within the camera head field of view to camera 336. The camera 236 may be an auto focusing USB camera that is coupled to a motion control system, such as shown in FIG. 16. General motion control and positioning of the inspection scope 220 along its motion degrees $\Phi$, $\theta$ and T and camera image capture are performed as previously described with respect to the inspection scope embodiment 50.

The inspection scope 220 includes an external cooling system for inspection within a turbine 30 cool-down phase when the turbine section 30 still has an elevated temperature of up to approximately 150° C. As was described with respect to the inspection scope embodiment 50, the cooling system includes an air line 170 running in parallel to or within the bore scope 228 that expels cooling air obtained from a cooling air source through one or more functional cooling air exhaust ports, such as around the camera head 230.

The three motion degrees $\Phi$, $\theta$ and T in the blade/vane inspection scope 220 embodiment are sufficient to obtain complete images of the leading or trailing sides of all rotating turbine blades within a given row while the turbine rotor is spinning in turning gear mode. For example in FIG. 18 the leading side of each of the Row 1 turbine blades 44 can be inspected by the inspection scope 220 that is positioned in inspection port 50. As each individual blade rotates within the camera head 230 field of view its image is captured by the associated control system. A partial or full series of blade images can be obtained during a single rotor 40 rotation while the turbine 30 is in turning gear mode. A single camera head 230 field of view may not capture the full radial length an area of interest on a turbine blade. By repositioning the camera head tilt angle $\Phi$ or inserting/retracting the bore scope 228 along the T freedom degree the camera field of view can be repositioned radially along the blade or vane length. Images captured at different blade/vane radial positions can be combined to create an aggregate image of the entire blade. Similarly, an image of the trailing edge of each blade 44 in Row 1 can be captured by positioning an inspection scope 220 in turbine inspection port 52, as was done for the leading edges.

Exemplary Turbine Inspection Procedures

The camera inspection system of the present invention provides the capability of automatic positioning and image capture of an inspection camera field of view relative to an area of interest with a turbine, such as a gas turbine, without human intervention. After inspection scope positioning sequence information is provided to the system, subsequent inspections are repeatable by different inspection teams, regardless of their individual inspection scope positioning skill or inspection speed. Automated inspections can be completed quicker, with less likelihood of human-created errors, as compared to known inspection procedures. Further explanation of the inspection methods of the present invention will be with reference to inspection of an exemplary industrial gas turbine.

Inspection scope positioning sequence information may be obtained by installing an inspection scope embodiment of the present invention on a selected inspection port and orienting all controlled motions to an initialized or "start" position. A human inspector guides the inspection scope through the control system HMI, e.g., by use of a joystick or touch screen pad, through a navigated path within the turbine that is recorded within one or both the control system controllers/host computer. The navigation path is chosen to orient the inspection scope camera head field of view within area of interest without causing undesirable impact of the scope with turbine internal components.

The control system retains the navigation path information from the initial human-controlled inspection and can subsequently repeat the inspection scope positioning sequence for future inspection cycles on the same turbine or other turbines having the same internal structure. For example, a navigation path sequence can be performed on a single test turbine and the sequence can be communicated to other remote sites for use by inspection teams inspecting the same structure gas turbine located at that site. In the field, an inspection team may be concerned that a different gas turbine may have variations in internal structure from the original gas turbine. The field team may review the stored navigation path individual step by step, with local override to accommodate any path variations needed for the field installation turbine to perform an inspection, or may choose to program a new navigation path dedicated to the field location turbine.

Navigation paths alternatively can be determined in virtual space by a human inspector simulating a navigation path in a simulated turbine and recording the path for subsequent use in actual turbine inspections. As another alternative, a scope inspection simulation program can prepare a suggested inspection navigation path for review and approval by a human inspector.

A navigation path sequence can move the camera head field of view from one position of interest to another position of interest. For example, an inspection scope can be affixed to a combustor inspection port, whereupon the inspection system can capture and record images of internal components within the combustor, then move to the leading edge of Row 1 vanes, pass through those vanes and inspect the leading edge of Row 1 blades. If the turbine is in turning gear mode the camera head can record sequentially the same image for each blade during a single rotor rotation.

When in a navigation path position the camera head may be repositioned to obtain image information from different camera fields of view from the same reference point. The various images taken from the same reference point can be combined to obtain a composite or "stitched" view of the structural elements, or to take a virtual "tour" of any or all portions of the turbine interior.

Rather than move the inspection scope camera head field of view from one position to another, it is also possible to move the turbine component areas of interest within the field of view of a stationary camera head. For example, an inspection scope inserted between blade and vane rows can capture an image of each blade rotating within the camera field of view, whether the turbine is in turning gear mode or whether an operator manually "bumps" each blade of a completely stopped turbine rotor sequentially in front of the camera head.

Although various embodiments which incorporate the teachings of the present invention have been shown and described in detail herein, those skilled in the art can readily devise many other varied embodiments that still incorporate these teachings. For example, "optical images" of turbine internal component can be obtained in the visible light spectrum or in the infrared spectrum. The inspection scope motion degrees do not have to be limited to those exemplary motions enabled by the servo motors 104 (Ω), 110 (T), 124 (θ), 124 (Φ), and 140 (E). Scope motion does not have to be imparted by servo motors, and can include known alternative pneumatic or other motion control systems.

What is claimed is:

1. A system for non-contact internal inspection of power generation machinery, comprising:
   a base for affixation to a power generation machine inspection port;
   an inspection scope having a proximal end coupled to the base, and an extendable elongated body defining a central axis, extended and driven by a linear drive that is capable of remote control and actuation by a control system;
   a camera head coupled to a camera, having a field of view, the camera head coupled to the inspection scope distal the base, that are capable of remote control and image capture by a control system;
   an articulation drive, coupled to the camera head and the control system, that is capable of remote control and actuation by a control system, for articulating the camera head and field of view relative to the inspection scope central axis; and
   a control system coupled to the inspection scope linear and articulation drives and the camera, for automatically guiding and positioning the inspection scope and camera field of view along a pre-designated pre-recorded non-contact navigation path of linear and articulation drives actuation instructions within a power generation machine to an internal area of interest without human intervention and for capturing a camera image thereof without human intervention.

2. The system of claim 1, wherein the control system automatically and sequentially positions the camera field of view to plural areas of interest along the navigation path and captures respective images thereof.

3. The system of claim 2, wherein the sequential positioning and image capture is performed automatically without human intervention.

4. The system of claim 2, wherein the sequential positioning and image capture allows human intervention in at least one of the sequential positioning steps before proceeding to the next step along the navigation path.

5. The system of claim 2, wherein the inspection scope moves along the navigation path between sequential positions.

6. The system of claim 2, wherein the inspection scope remains static between sequential positions, the plural areas of interest within the machine move along the navigation path, and the controller causes the camera to capture images of the plural areas of interest when they are within the camera field of view.

7. The system of claim 2, wherein images of plural areas of interest are combined to produce a composite image.

8. The system of claim 1, wherein the control system stores respective images of an area of interest taken at plural times and allows said images to be overlaid for inspection comparison.

9. The system of claim 1, wherein the pre-recorded navigation path designation is selected from the group consisting of:
   human controlled positioning of an inspection scope within a power generation machine of the same type along a selected navigation path, and recording said navigation path for subsequent replication by an inspection scope control system;
   human controlled simulated positioning of a virtual inspection scope within a virtual power generation machine of the same type along a selected navigation path, and recording said navigation path for subsequent replication by an inspection scope control system; and
   simulated positioning of a virtual inspection scope and virtual power generation machine of the same type along a simulated selected navigation path without human intervention, and recording said navigation path for subsequent replication by an inspection scope control system.

10. A method for non-contact internal inspection of power generation machinery, comprising the steps of:
    providing an internal inspection system having:
    a base for affixation to a power generation machine inspection port;
    an inspection scope having a proximal end coupled to the base, and an extendable elongated body defining a central axis, extended and driven by a linear drive that are capable of remote control and actuation by a control system;
    a camera head coupled to a camera, having a field of view, the camera head coupled to the inspection scope distal the base, that is are capable of remote control and image capture by a control system;
    an articulation drive, coupled to the camera head and the control system, that is capable of remote control and actuation by a control system, for articulating the camera head and field of view relative to the inspection scope central axis; and
    a control system coupled to the inspection scope linear and articulation drives and the camera, for automatically guiding and positioning the inspection scope and camera field of view along a pre-designated pre-recorded non-contact navigation path of linear and articulation drives actuation instructions within a power generation machine of the type being inspected to an internal area of interest without human intervention and for capturing a camera image thereof without human intervention;

affixing the base to a power machine inspection port;

providing the pre-recorded non-impact navigation path to the control system; and inspecting the power machine by automatically positioning the inspection scope and camera field of view along the navigation path with the control system without human intervention and capturing a camera image thereof without human intervention.

11. The method of claim 10, wherein during the inspecting step the control system automatically and sequentially positions the camera field of view to plural areas of interest along the navigation path and captures respective images thereof.

12. The method of claim 11, wherein the inspecting step is performed automatically without human intervention.

13. The method of claim 11, wherein the sequential positioning and image capture steps within the inspecting step allow human intervention in at least one of the steps before proceeding to the next step along the navigation path.

14. The method of claim 11, further comprising moving the inspection scope along the navigation path between sequential positions during the inspecting step.

15. The method of claim 11, further comprising during the inspecting step:
maintaining the inspection scope in a static position with the control system;
moving the plural areas of interest within the machine along the navigation path; and
capturing images of the plural areas of interest as they move into the camera field of view, with the camera and the control system.

16. The method of claim 11, further comprising combining images selected from the group consisting of:
combining images of plural areas of interest and producing a composite image; and
combining images taken at plural times and overlaying the images.

17. The method of claim 10, wherein the pre-recorded navigation path is determined by a method selected from the group consisting of:
human controlled positioning of an inspection scope of the type used in the inspecting step along a selected navigation path within a power generation machine of the type being inspected, and recording said navigation path for subsequent replication by the control system;
human controlled simulated positioning of a virtual inspection scope of the type used in the inspecting step within a virtual power generation machine of the type being inspected along a selected navigation path, and recording said navigation path for subsequent replication by the control system; and
simulated positioning of a virtual inspection scope and virtual power generation machine of the type used in the inspecting step along a simulated selected navigation path without human intervention, and recording said navigation path for subsequent replication by the control system.

18. The method of claim 10, wherein the power machine is selected from the group consisting of industrial gas turbines, steam turbines and generators.

19. A method for non-contact inspecting an industrial gas turbine, comprising the steps of:
shutting down a gas turbine operation;
providing an internal inspection system having:
a base for affixation to an inspection port of the turbine;
an inspection scope having a proximal end coupled to the base, and an extendable elongated body defining a central axis, extended and driven by a linear drive that are capable of remote control and actuation by a control system;
a camera head coupled to a camera, having a field of view, the camera head coupled to the inspection scope distal the base, that is are capable of remote control and image capture by a control system;
an articulation drive, coupled to the camera head and the control system, that is capable of remote control and actuation by a control system, for articulating the camera head and field of view relative to the inspection scope central axis; and
a control system coupled to the inspection scope linear and articulation drives and the camera, for automatically guiding and positioning the inspection scope and camera field of view along a pre-designated pre-recorded non-contact navigation path of linear and articulation drives actuation instructions within the gas turbine to an internal area of interest without human intervention and for capturing a camera image thereof without human intervention;
cooling the gas turbine to an internal temperature of less than 150° C. (300° F.);
affixing the base to an inspection port of the gas turbine;
providing the pre-recorded non-impact navigation path to the control system;
inspecting the gas turbine by automatically positioning the inspection scope and camera field of view along the navigation path with the control system without human intervention and capturing a camera image thereof without human intervention; and
storing the camera image for review.

20. The method of claim 19, wherein the pre-recorded navigation path is determined by a method selected from the group consisting of:
prior human controlled positioning of an inspection scope of the type used in the inspecting step within the actual inspected gas turbine along a selected navigation path, and recording said navigation path for subsequent replication by the control system of the inspection scope used in the inspecting step;
prior human controlled positioning of an inspection scope of the type used in the inspecting step within another gas turbine having the same type of internal structure as the actual inspected gas turbine along a selected navigation path, and recording said navigation path for subsequent replication by the control system of the inspection scope used in the inspecting step;
human controlled simulated positioning of a virtual inspection scope of the type used in the inspecting step within a virtual power generation machine of the type being inspected along a selected navigation path, and recording said navigation path for subsequent replication by the control system of the inspection scope used in the inspecting step; and
simulated positioning of a virtual inspection scope and virtual power generation machine of the type used in the inspecting step along a simulated selected navigation path without human intervention, and recording said navigation path for subsequent replication by the control system of the inspection scope used in the inspecting step.

* * * * *